United States Patent [19]

Price

[11] Patent Number: 4,864,850
[45] Date of Patent: Sep. 12, 1989

[54] METHOD AND APPARATUS FOR CONTINUOUSLY MONITORING THE MOISTURE CONTENT OF A MATERIAL

[75] Inventor: Robert D. Price, Carmel, Ind.

[73] Assignee: Nabisco Brands, Inc., Parsippany, N.J.

[21] Appl. No.: 578,245

[22] Filed: Feb. 8, 1984

[51] Int. Cl.[4] .............................................. G01N 5/02
[52] U.S. Cl. .................................. 73/73; 73/61.1 R; 324/61 P
[58] Field of Search ..................... 73/73, 61.1 R, 61 R; 324/61 P, 61 R

[56] References Cited

U.S. PATENT DOCUMENTS

| | | | |
|---|---|---|---|
| 2,720,624 | 10/1955 | Gungst et al. | 73/61.1 R |
| 2,752,562 | 6/1956 | De Witte | 324/61 P |
| 3,508,435 | 4/1970 | Ivy | 73/61.1 R |
| 3,515,988 | 6/1970 | Shawhan | 73/61.1 R |
| 3,870,951 | 3/1975 | Brown et al. | 324/61 P |
| 4,048,844 | 9/1977 | Dunikowski et al. | 73/61.1 R |
| 4,266,195 | 5/1981 | Keefner et al. | 324/61 P |
| 4,266,425 | 5/1981 | Allport | 73/61 R |
| 4,429,273 | 1/1984 | Mazzagatti | 73/61.1 R |

Primary Examiner—William A. Cuchlinski, Jr.
Attorney, Agent, or Firm—Richard Kornutik

[57] ABSTRACT

A method and apparatus for the continuous monitoring of the moisture content of a two-component material or product, such as margarine. The method and apparatus enables the continuous monitoring of the moisture content of the material through the generation of an electrical signal which is transmitted to a suitable data logging system wherein the electrical signal is converted into moisture content data and which stores the information for subsequent use. The apparatus for effectuating the continuous monitoring of the moisture content of the material, in which the material is treated while being conveyed through a flowline conduit in a processing system, includes a probe consisting of an elongated capacitor cell coated with or encased in a non-conductve material. The probe is inserted into the conduit in parallel with the direction of the flow of the material so as to be fully immersed therein.

15 Claims, 1 Drawing Sheet

METHOD AND APPARATUS FOR CONTINUOUSLY MONITORING THE MOISTURE CONTENT OF A MATERIAL

BACKGROUND OF THE INVENTION

1. Field of the Invention

The present invention relates to a method for the continuous monitoring of the moisture content of a two-component material or product, such as margarine, and more particularly, a method which enables the continuous monitoring of the moisture content of the material through the generation of an electrical signal which is transmitted to a suitable data logging system wherein the electrical signal is converted into moisture content data and which stores the information for subsequent use. The invention further contemplates the provision of an apparatus for implementing the inventive method for continuously monitoring the moisture content of the two-component material.

During the production and processing of various products which contain a certain proportion of water or moisture, and occasionally also some salt, for instance, such as margarine, it is of considerable importance to be able to provide for the continuous monitoring of the percentage of moisture contained in the margarine which is being processed, so as to allow for the control or regulating of the amount of moisture in the margarine.

Although numerous methods and different types of apparatus are currently existent and which are specifically designed to monitor the moisture content or percentages in various materials; for example, margarine, butter, fatty substances or petroleum products, none of these are completely satisfactory in providing for the continuous and practically instantaneous monitoring of the percent moisture in a margarine processing system. Thus, some of the methods which are employed for the measurement of moisture contained in margarine utilize line cells connected to measuring systems, wherein the cells are primarily designed for use with liquid products and which, as a result, are not entirely satisfactory in providing accurate information over the moisture content in margarine, particularly when the latter is in a semi-solid to solid state when processed in a continuous flowline system. Other moisture systems which are employed for the measurement or monitoring of moisture percentages in margarine necessitate laboratory testing procedures and are much more time consuming than would a continuous monitoring arrangement, while concurrently being subject to the disadvantage of only providing intermittent testing of a material which frequently is of a non-homogeneous consistency adversely affecting read-out accuracies. Consequently, moisture readings obtained through such earlier systems, which necessitate laboratory testing are subject to being somewhat inaccurate and do not allow for the continuous control over the contents of the material, such as margarine, being processed; whereas other continuous moisture monitoring methods and apparatus are not satisfactorily applicable to the continuous moisture testing of products such as margarine.

2. Discussion of the Prior Art

Allport U.S. Pat. No. 4,395,638 discloses a method for continuously determining the water and fat content of a material, such as butter, in which the density of the substance is instantaneously measured, as well as either the dielectric constant or radioactive backscatter intensity of the material to provide a suitable electrical signal. Allport accomplishes the foregoing by connecting a radioisotope density sensor, a capacitive moisture sensor in a velocimeter to a flow conduit through which the butter is conveyed. However, the rather complex system for the non-destructive method of determining the water and fat content of the material would not provide a continuous and accurate measurement of the moisture content of a generally semi-solid to solid product, which may also be of a non-homogeneous consistency, and in which the accuracy of the sensing measurement may be further adversely influenced by voids in the material flow towards the wall surfaces of the conduit through which the material flows. Consequently, the method described in Allport for measuring the moisture content of butter would not be particularly suitable for the continuous measurement of the moisture content of margarine being processed in a continuous flowline system analogous to that contemplated by the present invention.

Keefner et al. U.S. Pat. No. 4,266,195 discloses an apparatus and method for detecting the presence of water in a non-conductive medium, such as liquid or solid grease through measurement of the electrochemical potential difference between two dissimilar metals. Although the structure of the probe disclosed in Keefner et al. is of particular use in food, petrochemical and rendering industries, and would allow for the continuous measurement of moisture content in a material, it is primarily adapted to be immersed in a liquid flowline, and its positioning and structure would preclude the use thereof in a continuous flowline system for the processing of margarine wherein the product is of a semi-solid solid consistency and is of a generally non-homogeneous consistency, unlike the product in which this probe is immersed.

Schwartz U.S. Pat. No. 4,052,667 describes a moisture meter structure wherein a metallic probe is arranged within an annular chamber, the metallic probe and a dissimilar metal being located interiorly of an insulator, and with the entire assembly being hermetically sealed with respect to the surroundings. The probe is adapted to be immersed into a liquid and is connected to a meter which functions on the principle of a solid electrolyte battery in order to provide a readout over the moisture content of a liquid in a vessel in which the probe is immersed. The probe structure or moisture meter as described by Schwartz is not adapted to facilitate the continuous monitoring of the moisture content of a product, such as margarine, being processed and which may possess a semi-solid to solid consistency, and which may also be generally non-homogeneous. Consequently, the meter for the measurement of moisture as disclosed in by Schwartz is limited to the measurement of moisture in generally homogeneous materials which have a basically liquid consistency, and would not be readily adaptable to the present invention.

Briscoe et al. U.S. Pat. No. 4,242,906 discloses a thermocouple which is encased in a non-conductive shielding and is adapted to be immersed in a liquid so as to measure thermal changes. The probe disclosed therein, which may be used in a soil hygrometer, would not appear to be applicable to a system for the continuous monitoring of moisture in a product such as margarine.

Thompson U.S. Pat, No. 4,266,188 discloses a plurality of probes which are immersible in a petroleum flowline and are adapted to provide an electrical read-out representative of the measurement of the moisture content in a two-component liquid flow stream, which may consist of water-containing crude oil. There is no disclosure nor suggestion that the moisture probe disclosed by Thompson would be applicable to a process system for margarine which may have a semi-solid to solid consistency and which may also be constituted of a non-homogeneous mixture, so as to enable the probes to provide for an accurate moisture content readout.

Numerous other moisture content monitoring systems and methods are described; for example, in U.S. Pat. Nos. 3,253,458 to Katz et al., Carlson 4,097,743, Remke et al. 3,133,437. However, none of these patents, and extensive other publications in the technology pertaining to the measurement of moisture content in a substance, are deemed to be applicable to the continuous monitoring of moisture in a two-component substance, such as margarine, which essentially consists of water and a vegetable fat.

SUMMARY OF THE INVENTION

Accordingly, it is a primary object of the present invention to provide a method for the continuous monitoring of the moisture in a two-component material consisting essentially of water and of a vegetable fat.

It is a more specific object to provide a method for continuously monitoring the moisture content of an essentially two-component material of the type described herein, in which the components possess extensively differing dielectric constants, and wherein the moisture content is determined through an electrical signal generated as a function of the measurement of the composite dielectric constant of the material components.

Still another object of the present invention to provide a method for the continuous measurement of the moisture content of a two-component material wherein each component has a dielectric constant of a widely divergent value, and wherein the measurement of the composite dielectric constant of the components renders possible the measurement of the moisture to fat ratio of the material through an electrical signal generated as a function of the electrical capacitance of a capacitor cell probe.

Yet another object of the present invention is to provide a method for the measurement of the moisture content in a two-component material consisting essentially of water and a vegetable fat, and possibly some salt, such as margarine, wherein the measured moisture content is transmitted as an electrical signal to a data logging system for converting the electrical signal which is obtained as a function of moisture in the material to an analog value representative of percentage moisture and for storing the information for subsequent use in controlling the operation of a margarine flowline processing system.

Another object of the present invention is to provide a novel apparatus for implementing the inventive method for the continuous monitoring of the moisture content in a two-component material, such as margarine.

In essence, an inventive apparatus for effectuating the continuous monitoring of the moisture content of an essentially two- component material, such as margarine, and in which the material is treated while being conveyed through a flow line conduit in a processing system, includes a probe consisting of an elongated capacitor cell coated with or encased in a non-conductive material. The probe is inserted into the conduit in parallel with the direction of the flow of the material so as to be fully immersed therein. The probe is connected at the end thereof, externally of the flowline conduit to an electrical cable, wherein one conductor of the cable is grounded and connected to the conduit so as to electrically ground the entire flowline system, and the other conductor from the probe to a capacitor tester adapted to generate a frequency pulse train in correlation with the output capacitance of the capacitor cell probe. In turn, the output of the capacitor tester is connected to the input of a frequency counter possessing regularly-repeating gating periods, with the capacitor tester generating a number of pulses during each gating period of the frequency counter which is directly proportional to the output capacitance value of the capacitor cell probe. The frequency burst of the capacitor tester is thus proportional to the output capacitance of the capacitor cell probe as a function of the moisture content in the margarine or two-component material. In turn, the output of the frequency counter may be connected to a suitable signal converting unit, such as a microprocessor or computer, which will constitute a data logging unit collecting data, transmitting alarms in the event that the moisture content exceeds or drops below a prerequisite moisture percentage in the material, and maintaining records of production, thereby providing a continuous monitoring apparatus relative to the percentage of moisture in the margarine. The enclosure of the capacitor cell probe within a non-conductive material or sheath which, for example, may consist of polytetrafluoroethylene (Teflon), will render the probe insensitive to conductivity interferences caused by differences within the margarine emulsion. The non-conductive sheath over the probe will also preclude any effects on conductivity responsive to the presence of any salt and changes in density of the material. The capacitor cell probe is electrically insulated from the process system, as represented by the pipe or conduit in which it is mounted, through the interposition of an insulating sleeve or bushing insert which may be constituted of polytetrafluoroethylene (sold under the registered trademark Teflon), and with the space in an elbow of the conduit in which the probe is mounted being filled by means of the insulating insert so as to prevent any entrapment of material passing therethrough.

BRIEF DESCRIPTION OF THE DRAWINGS

Reference may now be had to the following detailed description of an exemplary embodiment of an apparatus for the continuous monitoring of the moisture content of a two-component material, such as margarine, taken in conjunction with the accompanying drawings; in which.

Figure 1:
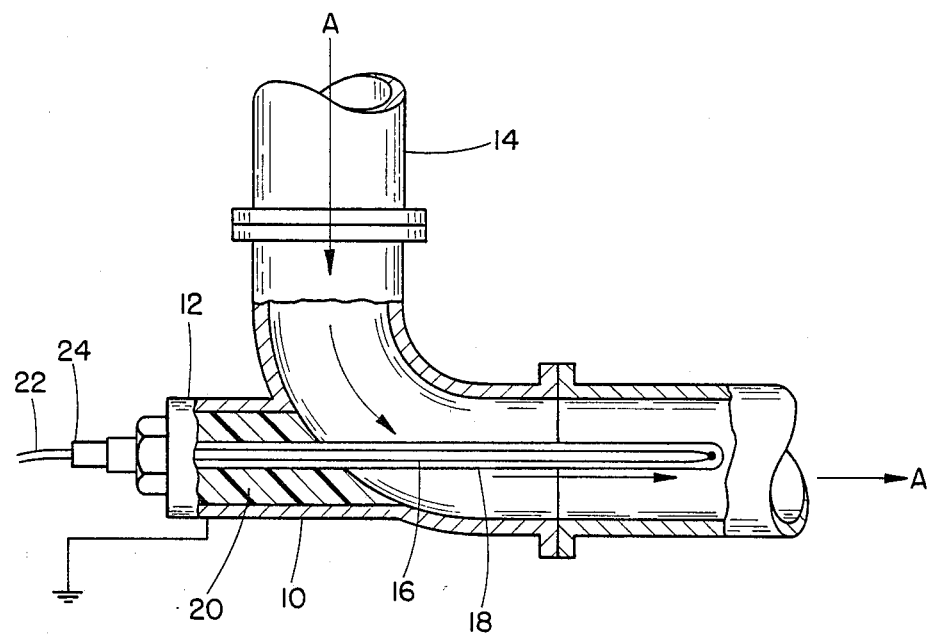
FIG. 1 illustrates a generally diagrammatic, partly sectioned representation of a capacitor cell probe for the monitoring of the moisture content in margarine which is conveyed through a conduit of a flowline processing system.

Referring now in detail to the drawings, and particularly FIG. 1, a moisture content monitoring unit 10 may incorporate a metal housing 12 which, if desired, may be an integral component of a conduit 14 forming a component of a process flowline for margarine which is conveyed in the direction of arrows A through the processing system. In order to provide an accurate reading the moisture content of the margarine, the latter of which is essentially a two-component material consisting of water and a vegetable fat, the unit 10 is positioned in the flowline and may constitute an elbow of the conduit 14. Arranged within the housing 12 is an elongated probe 16 consisting of a capacitor cell and which extends coaxially with the lower horizontal run of the conduit 14 so as to be fully immersed within the material conducted therethrough in the direction of arrows A.

Figure 2:
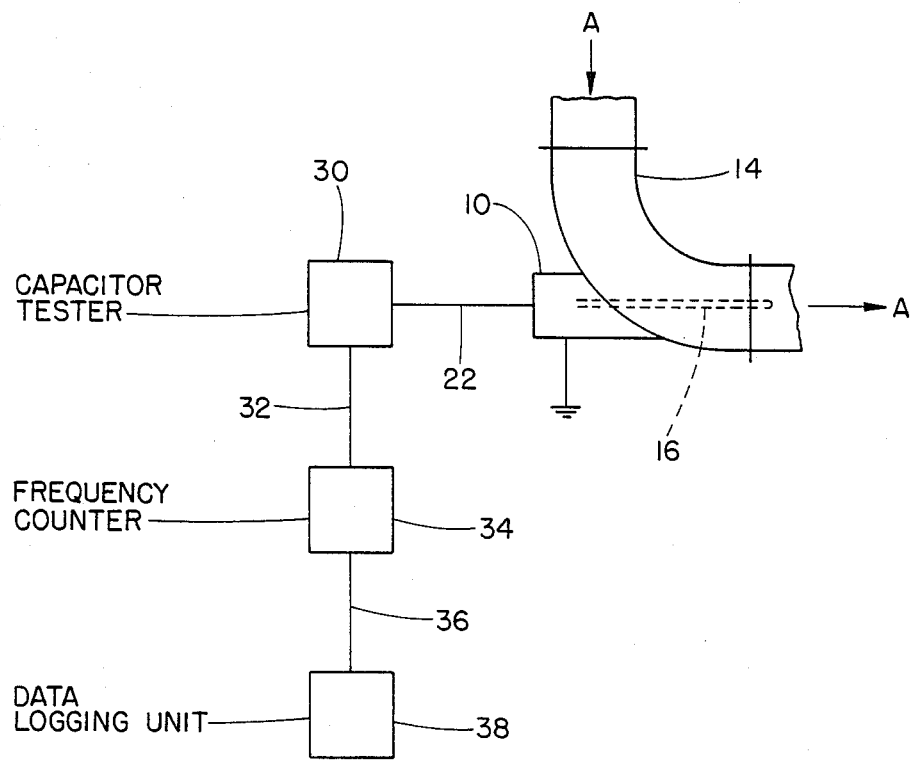
FIG. 2 illustrates a generally schematic circuit block diagram of the monitoring apparatus for testing the moisture content of a two-component material, such as margarine.

The capacitor cell probe 16 is coated with or encased by a suitable electrically insulating material, which may be in the form of a sheath 18, and which is preferably constituted of polytetrafluoroethylene (Teflon). The capacitor cell extends outwardly of the housing 12, while being electrically insulated therefrom through the provision of an insert 20 formed of an electrically insulating material such as polytetrafluoroethylene, which also fills the inner space of the housing 12 so as to avoid the collection of any material conveyed through the conduit 14 due to the presence of socalled "dead zones". An electrical cable 22 has one conductor thereof connected to a terminal end 24 of the capacitor cell probe 16, while a further conductor of the cable 22 is connected to the housing 12 and is grounded so as to ground the flowline processing system. The insulating sheathing 18 about the capacitor cell probe 16 prevents any contact between the probe and the material being processed in the conduit 14 so as to inhibit any conductivity interferences due to emulsion differences within the material, and the possible effects of any salt in the material The conductor which is connected to the terminal 24 of the capacitor cell probe 16, as illustrated in FIG. 2 of the drawings, connects to the input of a capacitor tester 30 which, for example, may be a C Probe II capacitor tester commercially available from International Instrumentation, Inc., although other suitable capacitor testers may be readily employed in the present arrangement. The capacitor tester 30 should be coupled as closely as possible to the probe 16 in order to reduce any capacitance effects of the connecting wires therebetween.

The capacitor tester 30 generates a pulse sequence at a rate which is directly proportional to the output value of the capacitor cell probe 16.

A line 32 connects the output of the capacitor tester 30 to the input of a frequency counter 34 having regularly repeating gating periods, and with the capacitor tester 30 generating a number of pulses during each gating period of the frequency counter 34 which is directly proportional to the output value of the capacitor cell probe 16. Preferably, this line 32 should be a low impedance line, such as a 75-ohm coaxial cable. The frequency burst of the capacitor tester 30 is also proportional to the input capacitance of the capacitor cell probe 16 as a function of the moisture content of the material being processed through the conduit 14.

The output of the frequency counter 34 is connected through a conductor 36, which may be a 75 ohm coaxial cable, with the input of a suitable computer or microprocessor data logging system 38, wherein the signal from the frequency counter 34 is converted into data so as to signify percent moisture in the material, and to store the information obtained for subsequent use.

The operation of the inventive apparatus for the continuous monitoring of the moisture content of a two-component material, such as margarine which consists essentially of water and a vegetable fat, is substantially as follows:

The capacitance cell probe 16 is introduced into the flow conduit 14 through the housing 12, and fastened therein by means of a suitable locking nut while being electrically isolated from the conduit and the material flowing through the conduit 14 by means of the insulating sheath 18 and the insulating insert 20. The capacitor cell probe acts as a coaxial capacitor which is terminated by the center probe 16 and the exterior of the conduit 14 which are connected to ground. The output capacitance of the capacitor cell probe 16 is largely dependent upon the composition of the material being conducted through the conduit 14. In this instance, the margarine which is being processed is constituted primarily of a vegetable fat having a dielectric constant of approximately 2 to 5 and of water which has a dielectric constant of about 78. This large differential between the dielectric constants of the components of the margarine renders it possible to measure the moisture to fat ratio as a function of the capacitance of the capacitor probe.

The foregoing is effected through the capacitor tester 30 which generates a frequency burst directly proportional to the input capacitance from the capacitor cell probe 16. The output signal from the capacitor tester is conducted to the remotely located frequency counter 34 through the conductor 32. The signal which is emitted from the frequency counter 34 is dependent upon the frequency pulse train generated by the capacitor tester generated by the capacitor tester in correlation with the capacitance of the capacitor cell, the frequency counter having regular gating periods and wherein the number of pulses generated by the capacitor tester through each gating period of the frequency counter is directly proportional with the value of the capacitor cell as a function of the moisture content of the two-component material.

The microprocessor or computer 38 converts the signals received from the frequency counter 34 into data representative of the moisture content in the material, such as converting the signals into percentage of moisture in the margarine, and may be adapted to transmit alarms in the event that the moisture content within the margarine deviates from predetermined norms, and may also be adapted to maintain production records and to store the information for subsequent use.

The foregoing allows for the continuous monitoring of the percent of moisture in a margarine process flow at a greater degree of accuracy, and providing instantaneous information as to the moisture content Moreover, the system or the monitoring of the moisture in margarine is adapted to operate at extremely high pressures, and is fully effective even when the margarine being conducted through the conduit 14 is in a semi-solid to solid state and represents a non-homogeneous mixtures. Furthermore, the sheathing of the capacitor cell probe with the electrically insulative material renders the probe insensitive through conductivity interferences which may be encountered due to the material emulsion differences. The entire monitoring probe assembly is also readily disassembled and may be easily cleaned, while being replaced by a similar probe arrangement, thereby greatly reducing any "down time" of the moisture testing system.

Additionally, the invention provides a monitoring arrangement which provides a good instantaneous correlation with laboratory tests on any products which are uniform in nature.

While there has been shown and described what are considered to be preferred embodiments of the invention, it will of course be understood that various modifications and changes in form or detail could readily be made without departing from the spirit of the invention. It is therefore intended that the invention be not limited to the exact for and detail herein shown and described, nor to anything less than the whole of the invention herein disclosed as hereinafter claimed.

What is claimed is:

1. A method of continuously monitoring the moisture content of an essentially two-component material wherein said components have extensively differing dielectric constants, one said component being water and the other component consisting of a vegetable fat; comprising the steps of:
   (a) conducting a generally continual flow of said two-component material through a conduit;
   (b) positioning a probe comprising a capacitor cell in said conduit so as to be fully immersed in said two-component material for continuously measuring the composite dielectric constant of said material;
   (c) providing an electrical connection between said capacitor cell and a capacitor tester for continuously generating a frequency pulse train in correlation with the capacitance of said capacitor cell;
   (d) connecting the output of said capacitor tester to the input of a frequency counter having regularly repeating gating periods, said capacitor tester generating a number of pulses during each gating period of said frequency counter which is directly proportional to the value of the capacitor cell, wherein the frequency burst of said capacitor tester is proportional to the input capacitance of the capacitor cell as a function of the moisture content of said material and;
   (e) conducting the output signals of said frequency counter to means converting said signals into data indicative of the moisture content in said two-component material.

2. A method as claimed in claim 1, wherein the output of said capacitor cell is a function of the differential between the dielectric constant of water and the dielectric constant of the vegetable fat in said two-component material.

3. A method as claimed in claim 2, wherein the water in said two-component material has a dielectric constant of about 78 and the vegetable fat has a dielectric constant of about 2 to 5, said capacitor cell probe providing a capacitive output to said capacitor tester by measuring the differential between the dielectric constants of said material.

4. A method as claimed in claim 1, wherein said signal converting means comprises a microprocessor.

5. A method as claimed in claim 1, wherein said conduit is a component of margarine process flowline.

6. An apparatus for continuously monitoring the moisture content of an essentially two-component material wherein said components have extensively differing dielectric constants, one said component being water and the other component consisting of a vegetable fat; comprising: conduit means for conveying a continuous flow of said two-component material; a capacitor cell probe being positioned within said conduit, said probe being continually immersed in said two-component material for continuously measuring the composite dielectric constant of said material; a capacitor tester arranged externally of said conduit means, said capacitor tester being electrically connected with said capacitor cell probe, said capacitor tester continuously generating a frequency pulse train in correlation with the capacitance of said capacitor cell; a frequency counter having an input connected with the output of said capacitor tester, said frequency counter having regularly repeating gating periods, said capacitor tester generating a number of pulses during each gating period of said frequency counter which is directly proportional to the value of the capacitor cell, the frequency burst of said capacitor tester being proportional to the input capacitance of the capacitor cell; and means connected to the output of said frequency counter for converting the output signals from said frequency counter into data indicative of the moisture content in said two-component material.

7. An apparatus as claimed in claim 6, wherein the output of said capacitor cell is a function of the differential between the dielectric constant of water and the dielectric constant of the vegetable fat in said two-component material.

8. An apparatus as claimed in claim 7, wherein the water in said two-component material has a dielectric constant of about 78 and the vegetable fat has dielectric constant of about 2 to 5, said capacitor cell probe providing a capacitive output to said capacitor tester by measuring the differential between the dielectric constants of said two-component material.

9. An apparatus as claimed in claim 6, wherein said signal converting means comprises a microprocessor.

10. An apparatus as claimed in claim 6, wherein said conduit is a component of a margarine processing flowline.

11. An apparatus as claimed in claim 10, comprising an electrical conductor interconnecting said capacitor cell probe with said capacitor tester, and another conductor being connected to said conduit and forming a connection with ground.

12. An apparatus as claimed in claim 6, said capacitor cell probe comprising an elongate element extending into said conduit; and an electrically-insulating sheath encompassing said probe inhibiting contact with said two-component material so as to prevent conductivity interferences.

13. An apparatus as claimed in claim 12, said electrically-insulating sheath comprising a polytetrafluoroethylene coating on said probe.

14. An apparatus as claimed in claim 6, comprising means for electrically insulating said capacitor cell probe from said conduit.

15. An apparatus as claimed in claim 14, said insulating means comprising a polytetrafluoroethylene insert in said conduit encompassing one end of said probe and positioning the probe in electrically-insulated relationship with the inner conduit walls.

* * * * *